United States Patent
Powers et al.

(10) Patent No.: US 7,521,427 B2
(45) Date of Patent: Apr. 21, 2009

(54) PEPTIDYL ALLYL SULFONES

(75) Inventors: James C. Powers, Atlanta, GA (US); Marion Gabriele Gotz, Elmhurst, IL (US)

(73) Assignee: Georgia Tech Research Corporation, Atlanta, GA (US)

( * ) Notice: Subject to any disclaimer, the term of this patent is extended or adjusted under 35 U.S.C. 154(b) by 411 days.

(21) Appl. No.: 11/270,404

(22) Filed: Nov. 9, 2005

(65) Prior Publication Data

US 2006/0241057 A1   Oct. 26, 2006

Related U.S. Application Data

(60) Provisional application No. 60/626,237, filed on Nov. 9, 2004.

(51) Int. Cl.
*C07K 5/06* (2006.01)
*C07K 5/062* (2006.01)

(52) U.S. Cl. .............................. 514/18; 514/19; 530/331
(58) Field of Classification Search ....................... None
See application file for complete search history.

(56) References Cited

U.S. PATENT DOCUMENTS 4,144,228 A * 3/1979 Jones et al. .................. 530/302
5,145,837 A * 9/1992 Feyen et al. ................... 514/16

* cited by examiner

*Primary Examiner*—Anish Gupta
(74) *Attorney, Agent, or Firm*—Thomas, Kayden, Horstemeyer & Risley, LLP; Todd Deveau

(57) ABSTRACT

The present disclosure provides compositions for inhibiting proteases, methods for synthesizing the compositions, and methods of using the disclosed protease inhibitors. Aspects of the disclosure include peptidyl allyl sulfone compositions that inhibit proteases, for example cysteine proteases, either in vivo or in vitro.

9 Claims, No Drawings

PEPTIDYL ALLYL SULFONES

CROSS-REFERENCE TO RELATED APPLICATION

This application claims benefit of and priority to U.S. Provisional Patent Application No. 60/626,237 filed on Nov. 9, 2004, and which is incorporated by reference in its entirety where permissible.

STATEMENT REGARDING FEDERALLY SPONSORED RESEARCH OR DEVELOPMENT

Aspects of the work disclosed herein were support in part by the National Institutes of Health Grant No. 1 R01 GM061964-01. Therefore, the US government may have rights in the claimed subject matter.

BACKGROUND

1. Field of the Invention(s)

This invention relates generally to protease inhibitors and applications thereof, more specifically to peptide inhibitors of cysteine proteases, even more specifically to allyl sulfones, methods of their use, and methods of their production.

2. Related Art

Protease inhibitors are important therapeutics in the treatment of a variety of disease conditions including viral infections such as HIV infection. Proteases are enzymes that cleave proteins or peptides and are classified into several groups. For example, cysteine proteases form a group of enzymes involved in numerous disease states, and inhibitors of these enzymes can be used therapeutically for the treatment of diseases involving cysteine proteases.

Cysteine Proteases.

Cysteine proteases employ a thiolate residue, which performs a nucleophilic attack on the amide bond of the peptide backbone to form a tetrahedral intermediate. The intermediate collapses to release the first product and the resulting acyl enzyme then undergoes hydrolysis. Based on their sequence homology cysteine proteases are divided into several clans and families. Clan CA and clan CD contain the majority of cysteine proteases. The majority of cysteine proteases, such as papain, calpains, cathepsins, and cruzain belong to the clan CA. According to the crystal structure of papain, clan CA proteases are unique for their catalytic triad formed by Cys, His, and Asn. The oxyanion hole is created by a preceding Gln residue. Clan CA enzymes are inhibited by E-64, a natural inhibitor of cysteine proteases, and cystatin. The substrate specificity of clan CA enzymes is primarily controlled by the S2 enzyme subsite. Clan CD enzymes are unique for their lack of inhibition by E-64 and their specificity for the P1 amino acid residue. Even though clan CD is the smallest of the clans, it contains some very important enzymes. Among them are caspases, legumains, gingipains, clostripain, and separase.

Neural tissues, including brain, are known to possess a large variety of proteases, including at least two calcium-stimulated proteases termed calpains. Calpains are present in many tissues in addition to the brain. Calpain I is activated by micromolar concentrations of calcium while calpain II is activated by millimolar concentrations. In the brain, calpain II is the predominant form, but calpain I is found at synaptic endings and is thought to be the form involved in long term potentiation, synaptic plasticity, and cell death. Other $Ca^{2+}$ activated cysteine proteases may exist, and the term "calpain" is used to refer to all $Ca^{2+}$ activated cysteine proteases, including calpain I and calpain II. The terms "calpain I" and "calpain II" are used herein to refer to the micromolar and millimolar activated calpains, respectively, as described above. While calpains degrade a wide variety of protein substrates, cytoskeletal proteins seem to be particularly susceptible to attack. In some cases, the products of the proteolytic digestion of these proteins by calpain are distinctive and persistent over time. Since cytoskeletal proteins are major components of certain types of cells, this provides a simple method of detecting calpain activity in cells and tissues. Activation of calpains and/or accumulation of breakdown products of cytoskeletal elements have been observed in neural tissues of mammals exposed to a wide variety of neurodegenerative diseases and conditions. For example, these phenomena have been observed following ischemia in gerbils and rats, following stroke in humans, following administration of the toxins kainate, trimethyltin, or colchicine in rats, and in human Alzheimer's disease.

Other clan CA proteases, cruzain and rhodesain, are essential for the development and survival of the protozoan parasites *Trypansoma cruzi* and *T. brucei*, respectively. *T. cruzi* causes Chagas' disease in humans in South and Central America, whereas *T. brucei* causes sleeping sickness in humans in large areas of central and southern Africa. Current drug therapies are accompanied by serious side effects and widespread resistance. Thus, the need of new medicinal agents is urgent.

Cathepsins comprise a large family of lysosomal cysteine proteases and are involved in the degradation of host connective tissues, the generation of bioactive proteins and antigen processing. They have been implicated in a variety of disease states such as rheumatoid arthritis, muscular dystrophy, and tumor metastasis. The high similarity in the substrate specificity among the individual cathepsins presents a challenge in finding selective and thus effective cathepsin inhibitors.

Cysteine Protease Inhibitors.

To date, a structurally diverse variety of cysteine protease inhibitors have been identified. Palmer, (1995) J. Med. Chem., 38, 3193, incorporated herein by reference, discloses certain vinyl sulfones, which act as cysteine protease inhibitors for cathepsins B, L, S, O2 and cruzain. Other classes of compounds, such as aldehydes, nitriles, α-ketocarbonyl compounds, halomethyl ketones, diazomethyl ketones, (acyloxy) methyl ketones, ketomethylsulfonium salts and epoxy succinyl compounds have also been reported to inhibit cysteine proteases. See Palmer, id, and references cited therein. However, most of these known inhibitors are not considered suitable for use as therapeutic agents in animals, especially humans, because they suffer from various shortcomings. These shortcomings include lack of selectivity, cytotoxicity, poor solubility, and overly rapid plasma clearance. Many irreversible cysteine protease inhibitors have been described in the review by Powers, Asgian, Ekici, and James (2002) Chemical Reviews, 102, 4639. See Powers, id, and references cited therein, all of which are incorporated herein by reference.

Among the most effective inhibitors are the vinyl sulfones and α,β-unsaturated carbonyl derivatives. Hanzlik, (1984) J. Med. Chem., 27, 711 has replaced the carbonyl group of a good substrate with a Michael acceptor moiety, which can trap the enzymatic nucleophile (Ser-OH or Cys-OH) without altering the structural features required for enzyme recognition and binding. The fumarate derivative of the epoxy succinate E-64c, which is one of the first Michael acceptor inhibitors reported, extends the α,β-unsaturated carbonyl by an additional carbonyl for possible structural recognition and binding requirements within the enzyme active site. The fumarate derivative of E-64c (trans-HOOCCH=CH—CO-Leu-NH(CH$_2$)$_2$CH(CH$_3$)$_2$) inhibits cathepsin B (k$_{app}$=625 M$^{-1}$s$^{-1}$), cathepsin H, and cathepsin L (k$_{app}$=2272 M$^{-1}$s$^{-1}$) irreversibly. Both the fumarate analog of E-64c and the epoxide parent compound do not inhibit clan CD proteases, and are therefore specific for clan CA cysteine proteases. Caspases, legumains, gingipains and clostripain are members of clan CD, while papain, cathepsins, and calpains are members of clan CA. Therefore, because of the aforementioned deficiencies in the art, there is a need for new compounds and methods for inhibiting proteases, in particular cysteine proteases.

SUMMARY

Aspects of the present disclosure provide compositions for inhibiting proteases, methods for synthesizing the compositions, and methods of using the disclosed protease inhibitors. The compositions described herein can inhibit proteases, for example cysteine proteases, either in vivo or in vitro, by contacting a cysteine protease with a peptidyl allyl sulfone. The disclosed compounds, pharmaceutically acceptable salts thereof, pharmaceutically acceptable derivatives thereof, prodrugs thereof, or combinations thereof can be used to treat disease or pathological conditions related to the activity of proteases associated with a specific disease or condition. Such treatable conditions include viral infections, stroke, neurodegenerative disease, and inflammatory disease, among others.

Methods disclosed herein for treating diseases include administering an effective amount of a peptidyl allyl sulfone to a host, in particular a mamalian host, in need thereof to inhibit or reduce protease activity in the host, particularly cysteine protease activity, more particularly activity of the calpains, cathepsins, papain, and the parasitic proteases cruzain and rhodesain. One or more peptidyl allyl sulfones of the present disclosure can also be used alone or in combination with each other, other protease inhibitors, or another therapeutic agent including anti-viral compounds such as anti-viral nucleosides including nucleoside analogs.

One aspect of the disclosure provides peptidyl allyl sulfone compositions, for example a compound or pharmaceutically acceptable salt or pharmaceutically acceptable derivative thereof according to Formula I below. In some aspects of the present disclosure, peptidyl allyl sulfone inhibitors are specific for cysteine proteases and do not inhibit serine proteases or aspartyl proteases. In another aspect of the present disclosure, these peptidyl allyl sulfone compounds potently and specifically inhibit clan CA cysteine proteases. Although the compounds of the present disclosure are usually specific for cysteine proteases of clan CA, they are also inhibitors of other proteases. Exemplary differences between peptidyl allyl sulfones disclosed herein and other cysteine protease inhibitors include different mechanisms of inhibition of the cysteine residue and the binding modes.

Some peptidyl allyl sulfones of the present disclosure can be constructed to selectively inhibit individual cysteine proteases or groups of cysteine proteases. These peptidyl allyl sulfones can, for example, contain aliphatic residues in the P2 site. Such peptidyl allyl sulfones are potent inhibitors of calpains. Peptidyl allyl sulfone calpain inhibitors are useful for the treatment of cell injury due to ischemic stroke, physical damage, and hypoxia. Thus, another aspect provides a method of treating cell injury due to ischemic stroke, physical damage, and hypoxia including administering an effective amount of a peptidyl allyl sulfone to a patient in need thereof. Such patients can include any mammal, for example a mammal exhibiting symptoms characteristic of a protease related pathology or disease condition.

Another aspect of the present disclosure provides a peptidyl allyl sulfone composition containing a phenylalanine and leucine in the P1 and P2 position respectively. Peptidyl allyl sulfones having such a sequence inhibit cathepsins and can, therefore, treat cancer and muscular dystrophy. The same peptidyl allyl sulfones also inhibit the parasitic clan CA cysteine proteases cruzain and rhodesain. Since parasite development is controlled by cruzain and rhodesain, administering an effective dose of the appropriate peptidyl allyl sulfone to an infected mammal, including primates provides a treatment of Chagas' disease or sleeping sickness.

In another aspect, a method is disclosed herein to identify proteolytic enzymes and a method to prevent proteolysis.

Other compositions, methods of use of the compositions and methods of their manufacture and advantages of the disclosed compositions and methods will be or become apparent to one with skill in the art upon examination of the following detailed description. It is intended that all such additional compositions, methods, and advantages be included within this description, be within the scope of the present invention, and be protected by the accompanying claims.

DETAILED DESCRIPTION OF THE INVENTION

The present disclosure may be understood more readily by reference to the following detailed description and the Examples included therein.

Before the present compounds, compositions and methods are disclosed and described, it is to be understood that this disclosure is not limited to specific synthetic methods, specific pharmaceutical carriers, or to particular pharmaceutical formulations or administration regimens, as such may, of course, vary. It is also to be understood that the terminology used herein is for the purpose of describing particular embodiments only and is not intended to be limiting.

Cysteine Proteases.

The peptidyl allyl sulfone compositions provided herein inhibit enzymatic cleavage of proteins or peptides, or a combination thereof. Exemplary enzymes inhibited by peptidyl allyl sulfones include cysteine proteases, for example, calpains, cathepsins, cruzain and rhodesain.

The present disclosure includes all hydrates, solvates, complexes and prodrugs of the compounds of this disclosure. The term prodrug refers to a pharmacologically inactive compound that is converted to an active drug by a metabolic biotransformation. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of Formula I. Additional types of prodrugs are also encompassed. For instance, free carboxyl groups can be derivatized as amides or alkyl esters. The amide and ester moieties may incorporate groups including but not limited to ether, amine and carboxylic acid functionalities. Free hydroxy groups may be derivatized using groups including but not limited to hemisuccinates, phosphate esters, dimethylaminoacetates, and phosphoryloxymethyloxycarbonyls, as outlined in D. Fleisher, R. Bong, B. H. Stewart, Advanced Drug Delivery Reviews (1996) 19, 115. Carbamate prodrugs of hydroxy and amino groups are also included, as are carbonate prodrugs and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in R. P. Robinson et al., J. Medicinal Chemistry (1996) 39, 10.

The subject disclosure also includes isotopically-labelled compounds, and the pharmaceutically acceptable salts thereof, which are identical to those recited in Formula I, but for the fact that one or more atoms are replaced by an atom having an atomic mass or mass number different from the atomic mass or mass number usually found in nature. Examples of isotopes that can be incorporated into compounds of the present disclosure include isotopes of hydrogen, carbon, nitrogen, oxygen, phosphorous, fluorine and chlorine. Compounds of the present disclosure, prodrugs thereof, and pharmaceutically acceptable salts of said compounds or of said prodrugs, which contain the aforementioned isotopes and/or other isotopes of other atoms are within the scope herein. Certain isotopically-labelled compounds of the present disclosure, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of Formula I of this disclosure and prodrugs thereof can generally be prepared by carrying out the procedures disclosed in the Schemes and/or in the Examples and Preparations below, by substituting a readily available isotopically labeled reagent for a non-isotopically labeled reagent.

If a chiral center or another form of an isomeric center is present in a compound of the present invention, all forms of such isomer or isomers, including enantiomers and diastereomers, are intended to be covered herein. Inventive compounds containing a chiral center may be used as a racemic mixture or an enantiomerically enriched mixture. Alternatively, the racemic mixture may be separated using well-known techniques, and an individual enantiomer may be used alone. An enantiomerically enriched mixture means a mixture having greater than about 50% of a single enantiomer. In cases in which compounds have unsaturated carbon-carbon double bonds, both the cis (Z) and trans (E) isomers are within the scope of this invention. The compositions of the present disclosure can be substantially optically pure. Substantially optically pure means a composition having greater than 90%, preferably greater than 95%, most preferably greater than 98% of a single optical isomer.

It must be noted that, as used in the specification herein and the appended claims, the singular forms "a," "an" and "the" include plural referents unless the context clearly dictates otherwise. Thus, for example, reference to "an aromatic compound" includes mixtures of aromatic compounds, reference to "a pharmaceutical carrier" includes mixtures of two or more such carriers, and the like.

Nomenclature and Definitions.

In discussing the interactions of peptides with cysteine proteases, we have utilized the nomenclature of Schechter and Berger [*Biochem. Biophys. Res. Commun.* 27, 157-162 (1967); incorporated herein by reference]. The individual amino acid residues of a substrate or inhibitor are designated P1, P2, etc., and the corresponding subsites of the enzyme are designated S1, S2, etc. The scissile bond of the substrate is P1-P1'. The most important recognition subsites of cysteine proteases are S1 and S2.

Amino acid residues and blocking groups are designated using standard abbreviations (see J. Biol. Chem. 260, 14-42 (1985) for nomenclature rules, incorporated herein by reference). An amino acid residue (AA) in a peptide or inhibitor structure refers to the part of the structure —NH—CHR$_1$—CO—, where R$_1$ is the side chain of the amino acid residue AA. It will be appreciated that at least one of the amino acid residues of the allyl sulfones of the invention may be substituted by one of the well known non-naturally occurring amino acid residues. Alterations such as these may serve to increase the stability, bioavailability and/or inhibitory action of the peptides of the present disclosure. Moreover, any of the peptidyl allyl sulfones described herein may, additionally, have a non-peptide macromolecular carrier group covalently attached to their amino and/or carboxy termini. Such macromolecular carrier groups may include, for example, lipid-fatty acid conjugates, polyethylene glycol, or carbohydrates. The term MeAA describes an N-methylated amino acid, as for example MePhe, which is phenylalanine, where the nitrogen is substituted with a methyl group.

The following figure shows two examples of a peptidyl allyl sulfone. A vinyl sulfone (AA-VS) (structure bottom) is a modified alpha-amino acid residue (structure left) where the amino acid carbonyl is replaced by a vinyl sulfone moiety. An amino acid allyl sulfone (AA-AS) (structure right) is a modified alpha-amino acid residue (structure left) where the amino acid carbonyl is replaced by an allyl sulfone moiety. As a result the alpha-carbon is sp$^2$ hybridized.

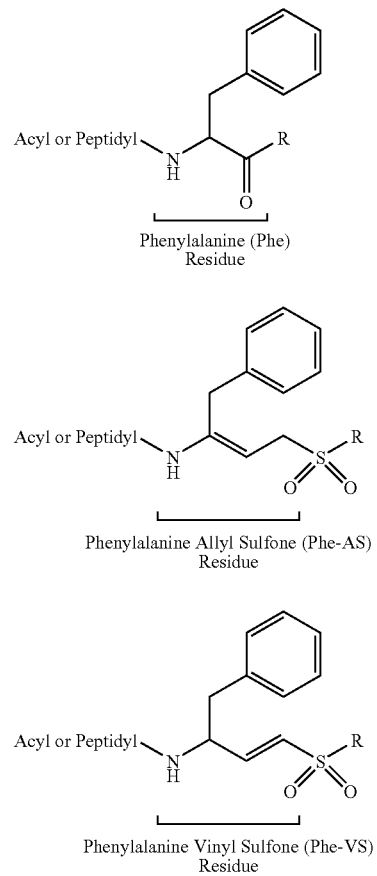

Phenylalanine (Phe) Residue

Phenylalanine Allyl Sulfone (Phe-AS) Residue

Phenylalanine Vinyl Sulfone (Phe-VS) Residue

Therefore, substituting the carbonyl of a phenylalanine residue with an allyl sulfone moiety converts a phenylalanine residue (Phe) to a phenylalanine allyl sulfone residue, which will be abbreviated as Phe-AS.

The complete structures of three peptidyl allyl sulfones and their abbreviated structures are shown in the following figure.

| Structure | Abbreviation |
|---|---|
| 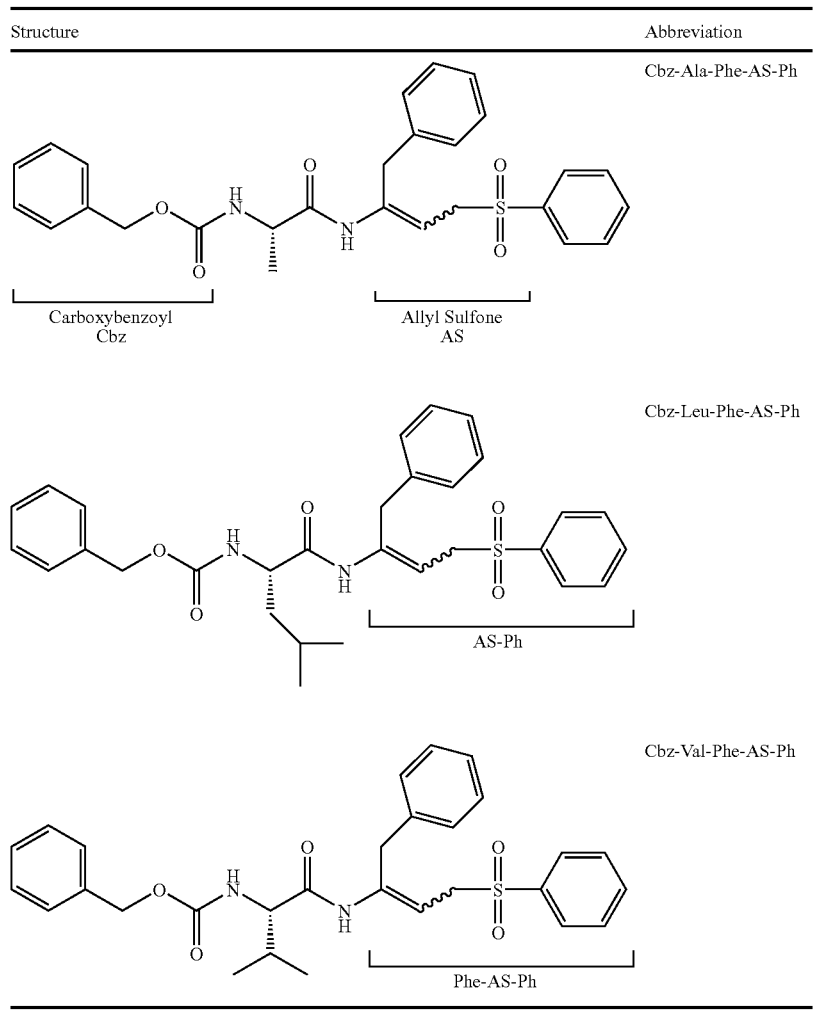 | Cbz-Ala-Phe-AS-Ph

Cbz-Leu-Phe-AS-Ph

Cbz-Val-Phe-AS-Ph |

There can be two structural isomers at the allyl sulfone double bond moiety, if the appropriate substituents are present, the trans isomers E and Z. The E and Z terminology applies to compounds that contain a C=C double bond with more than two substituents. The Cahn-Prelog-Ingold selection rules are used to assign priorities to the various substituents. If the two substituents with the highest priority are on the same side, the double bond is given the designation Z (from zusammen) and E (from entgegen), if they are on opposite sides.

The wavy line in the above structure indicates that the double bond moiety could be either E, Z, or a mixture of both.

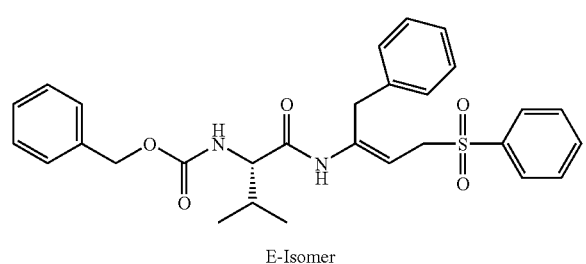

E-Isomer

-continued

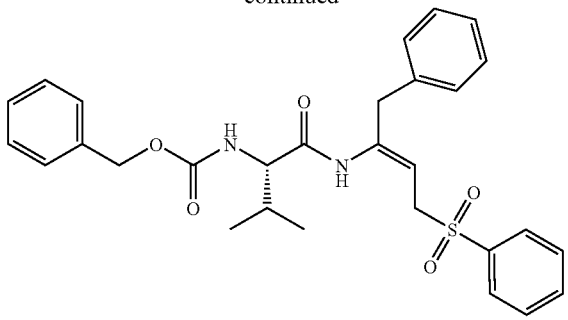

Z-Isomer

The term "amino," as used herein, refers to —NH$_2$ or derivatives thereof formed by independent replacement of one or both hydrogen atoms thereon with a substituent or substituents independently selected from alkyl, alkanoyl, aryl, arylalkyl, cycloalkyl, cycloalkylalkyl, heteroaryl, heteroarylalkyl, and an amino protecting group.

The term "$C_{1-10}$ acyl," as used herein, refers to a $C_{1-10}$ alkyl group, as defined herein, having an attached carbonyl group.

The term "$C_{1-10}$ alkoxy," as used herein, refers to a $C_{1-10}$ alkyl group, as defined herein, attached to the parent molecular group through an oxygen atom.

The term "$C_{1-10}$ alkyl" as used herein refers to a branched or unbranched hydrocarbon group of carbon atoms, such as methyl, ethyl, n-propyl, isopropyl, n-butyl, isobutyl, 1-butyl, and the like, or branched or unbranched hydrocarbon groups of carbon atoms that either contain double or triple carbon bonds.

The term "$C_{1-10}$ alkylamino," as used herein, refers to a $C_{1-10}$ alkyl group, as defined herein, to which is attached at least one amino substituent.

The term "$C_{3-15}$ cycloalkyl" as applied herein is meant to include cyclic hydrocarbon chains. Examples of these cyclic hydrocarbon chains include cyclopropane, cyclobutane, cyclopentane, cyclohexane, cycloheptane, cyclooctane, cyclononane, cyclodecane, cycloundecane, etc.

The term "$C_{2-12}$ dialkylamino," as used herein, refers to two $C_{1-10}$ alkyl groups, as defined herein, that are attached to an amino substituent.

The term "$C_{1-10}$ fluoroalkyl," as used herein, refers to a $C_{1-10}$ alkyl group, as defined herein, to which is attached at least one fluorine substituent.

The term "$C_{1-10}$ perfluoroalkyl," as used herein, refers to a $C_{1-10}$ alkyl group in which all of the hydrogen atoms have been replaced with fluorine atoms.

The term "biotinyl," as use herein, refers to biotin without the biotin carboxyl hydroxyl group.

By the term "effective amount" of a compound as provided herein is meant a nontoxic but sufficient amount of the compound to provide the desired utility. As will be pointed out below, the exact amount required will vary from subject to subject, depending on the species, age, and general condition of the subject, the severity of the condition or disease that is being treated, the particular compound used, its mode of administration, and the like. Thus, it is not possible to specify an exact "effective amount." However, an appropriate effective amount may be determined by one of ordinary skill in the art using only routine experimentation.

The term "pharmaceutically acceptable salt(s)", as used herein, unless otherwise indicated, includes salts of acidic or basic groups, which may be present in the compounds of Formula I. The compounds of Formula I that are basic in nature are capable of forming a wide variety of salts with various inorganic and organic acids. The acids that may be used to prepare pharmaceutically acceptable acid addition salts of such basic compounds of Formula I are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, TFA, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Those compounds of Formula I that are acidic in nature, are capable of forming base salts with various pharmacologically acceptable cations. Examples of such salts include the alkali metal or alkaline earth metal salts and particularly, the sodium and potassium salts.

The term "pharmaceutically acceptable derivative" refers to any homolog, analog, or fragment corresponding to the allyl sulfones of the present invention provided herein which inhibits protease activity and is relatively non-toxic to the subject or host.

The term "pharmaceutically acceptable" means a material that is not biologically or otherwise harmful and/or toxic, i.e., the material may be administered to an individual along with the selected allyl sulfone without causing any harmful and/or toxic biological effects or interacting in a deleterious manner with any of the other components of the pharmaceutical composition in which it is contained.

As used herein, and without limitation, the term "derivative" is used to refer to any compound that has a structure derived from the structure of the compounds of the present invention and whose structure is sufficiently similar to those disclosed herein and that, based upon that similarity, would be expected by one skilled in the art, to exhibit the same or similar activities and utilities as the claimed compounds.

The following abbreviations have also been used: AC, Acetyl; AFC, 7-amino-4-trifluoromethylcoumarin; AS, allyl sulfone; AMC, 7-amino-4-methylcoumarin; Boc, tert-butoxycarbonyl; Brij, polyoxyethylenelaurylether; Bzl, benzyl; CHAPS, 3-[(3-cholamidopropyl)dimethylammonio]-1-propanesulfonate; Cbz, Ph-CH$_2$OCO—; DCC, 1,3-dicyclohexylcarbodiimide; DMAP, 4-dimethylaminopyridine; DMF, N,N-dimethylformamide; DMSO, dimethylsulfoxide; DTT, dithiothreitol; EDC, 1-(3-dimethylaminopropyl)-3-ethylcarbodiimide hydrochloride; EtOAc, ethyl acetate; EtPh, Ethylphenyl; HEPES, N-2-hydroxyethylpiperazine-N'-2-ethanesulfonic acid; Hph, homophenylalanine; HOBt, 1-hydroxybenzotriazole; HRMS, high resolution mass spectrometry; iBCF, isobutyl chloroformate; IBX, iodooxybenzoic acid; IC, inhibitory concentration; Mu, morpholine urea; 2-Napth or 2Np, 2-naphthyl; NMM, 4-methylmorpholine; Np2,2-naphthylalanyl; Ph, phenyl; PhPr, Phenylpropyl; Pyr, pyridine; TFA, trifluoroacetic acid; THF, tetrahydrofuran; TLC, thin layer chromatography; VS, vinyl sulfone.

Compositions

One embodiment of the present disclosure provides peptidyl allyl sulfones having the following structural Formula I:

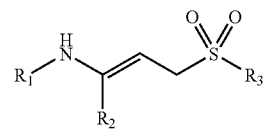

wherein, $R_1$ is selected from the group including, but not limited to, $M_1$-$AA_1$, $M_1$-$AA_2$-$AA_1$, and $M_1$-$AA_3$-$AA_2$-$AA_1$;

$M_1$ is selected from the group including, but not limited to, H, NH$_2$—CO—, NH$_2$—CS—, NH$_2$—SO$_2$—, X—NH—CO—, X$_2$N—CO—, X—NH—CS—, X$_2$N—CS—, X—NH—SO$_2$—, X$_2$N—SO$_2$—, X—CO—, X—CS—, X—, Y—SO$_2$—, Y—O—CO—, Y—O—CS—, 4-morpholine-CO—, N-methylpiperidine-CO—, piperazine-CO—, N-methylpiperazine-CO—, and biotinyl;

X is selected from the group including, but not limited to, H, $C_{1-10}$ alkyl, $C_{3-15}$ cyclized alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, pentafluorophenyl, phenyl monosubstituted with K, phenyl disubstituted with K, phenyl trisubstituted with K, naphthyl, naphthyl monosubstituted with K, naphthyl disubstituted with K, naphthyl trisubstituted with K, $C_{1-10}$ fluoroalkyl with an attached phenyl group, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached naphthyl group, $C_{1-10}$ alkyl with an attached naphthyl group substituted with K, $C_{1-10}$ alkyl with an attached phenoxy group, and $C_{1-10}$ alkyl with an attached phenoxy group substituted with K on the phenoxy group;

Y is selected from the group including, but not limited to, $C_{1-10}$ alkyl, $C_{3-15}$ cyclized alkyl, $C_{1-10}$ fluoroalkyl, $C_{1-10}$ alkyl substituted with J, $C_{1-10}$ fluoroalkyl substituted with J, 1-adamantyl, 9-fluorenyl, phenyl, phenyl monosubstituted with K, phenyl disubstituted with K, phenyl trisubstituted with K, naphthyl, naphthyl monosubstituted with K, naphthyl disubstituted with K, naphthyl trisubstituted with K, $C_{1-10}$ fluoroalkyl with an attached phenyl group, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached naphthyl group, $C_{1-10}$ alkyl with an attached naphthyl group substituted with K, $C_{1-10}$ alkyl with an attached phenoxy group, and $C_{1-10}$ alkyl with an attached phenoxy group substituted with K on the phenoxy group;

J is selected from the group including, but not limited to, halogen, $CO_2H$, OH, CN, $NO_2$, amino, $C_{1-10}$ alkoxy, $C_{1-10}$ alkylamino, $C_{2-12}$ dialkylamino, $C_{1-10}$ alkyl-O—CO—, $C_{1-10}$ alkyl-O—CO—NH—, and $C_{1-10}$ alkyl-S—;

K is selected from the group including, but not limited to, halogen, $C_{1-10}$ alkyl, $C_{1-10}$ perfluoroalkyl, $C_{1-10}$ alkoxy, phenoxy, $NO_2$, CN, OH, $CO_2H$, $CONH_2$, amino, $C_{1-10}$ alkylamino, $C_{2-12}$ dialkylamino, $C_{1-10}$ acyl, and $C_{1-10}$ alkoxy-CO—, and $C_{1-10}$ alkyl-S—;

$AA_1$, $AA_2$, and $AA_3$ are side chain blocked or unblocked amino acids with the L configuration, D configuration, or no chirality at the alpha-carbon, selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutanoic acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—$CH(CH_2CHEt_2)$-$CO_2H$, alpha-aminoheptanoic acid, $NH_2$—$CH(CH_2$-1-naphthyl)-$CO_2H$, $NH_2$—CH$(CH_2$-2-naphthyl)-$CO_2H$, $NH_2$—$CH(CH_2CH_2CH_2$-phenyl)-$CO_2H$, $NH_2$—$CH(CH_2$-cyclohexyl)-$CO_2H$, $NH_2$—CH$(CH_2$-cyclopentyl)-$CO_2H$, $NH_2$—$CH(CH_2$-cyclobutyl)-$CO_2H$, $NH_2$—$CH(CH_2$-cyclopropyl)-$CO_2H$, trifluoroleucine, 4-fluorophenylalanine, lysine substituted on the epsilon nitrogen with a biotinyl group, hexafluoroleucine,

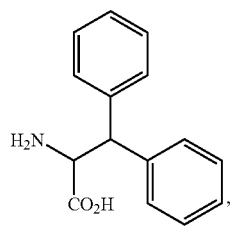

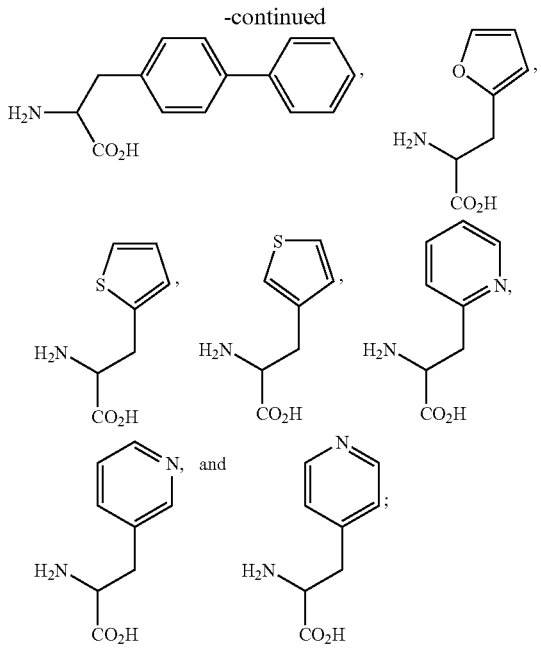

$R_2$ is selected from the group including, but not limited to, $C_{1-10}$ alkyl, $C_{1-10}$ perfluoroalkyl, $C_{1-10}$ alkyl substituted with Q, $C_{1-10}$ alkyl substituted with phenyl, $C_{1-10}$ alkyl with an attached phenyl substituted with K, $C_{1-10}$ alkyl substituted with naphthyl, $C_{1-10}$ alkyl with an attached naphthyl substituted with K, phenyl, phenyl substituted with K, naphthyl, naphthyl substituted with K, $C_{1-10}$ alkyl substituted with $CONH_2$, $C_{1-10}$ alkyl substituted with $CONHR_4$, $C_{1-10}$ alkyl substituted with $CO_2H$, $C_{1-10}$ alkyl substituted with $SO_2NH_2$, $C_{1-10}$ alkyl substituted with $SO_3H$, 2-furyl, 3-furyl, 2-thienyl, 3-thienyl, 2-furyl substituted with K, 3-furyl substituted with K, 2-thienyl substituted with K, 3-thienyl substituted with K, 2-furyl substituted with G, 3-furyl substituted with G, 2-thienyl substituted with G, 3-thienyl substituted with G, $C_{1-10}$ alkyl substituted with $CO_2R_5$, $CH_2CH_2SCH_3$, $CH_2$-3-indolyl, $C_{1-2}$ alkyl with an attached 2-furyl, $C_{1-2}$ alkyl with an attached 3-furyl, $C_{1-2}$ alkyl with an attached 2-thienyl, $C_{1-2}$ alkyl with an attached 3-thienyl, $C_{1-2}$ alkyl with an attached 2-furyl substituted with K, $C_{1-2}$ alkyl with an attached 3-furyl substituted with K, $C_{1-2}$ alkyl with an attached 2-thienyl substituted with K, $C_{1-2}$ alkyl with an attached 3-thienyl substituted with K, $C_{1-2}$ alkyl with an attached 2-furyl substituted with G, $C_{1-2}$ alkyl with an attached 3-furyl substituted with G, $C_{1-2}$ alkyl with an attached 2-thienyl substituted with G, $C_{1-2}$ alkyl with an attached 3-thienyl substituted with G, $CH_2$-2-imidazyl, $C_{1-10}$ alkyl substituted with G, $C_{1-10}$ alkyl with an attached phenyl substituted with G, $C_{1-10}$ alkyl with an attached naphthyl substituted with G, phenyl substituted with G, and naphthyl substituted with G;

$R_4$ is selected from the group including, but not limited to, $C_{1-10}$ alkyl and $C_{1-10}$ alkyl substituted with phenyl;

Q is selected independently from the group including, but not limited to, $C_{1-10}$ alkoxy, $C_{1-10}$ alkyl-S—, $C_{1-10}$ alkoxy substituted with phenyl, and $C_{1-10}$ alkyl-S— substituted with phenyl;

G is selected from the group including, but not limited to, amidino (—C(=NH)$NH_2$), guanidino (—NHC(=NH)$NH_2$), isothiureido (—S—C(=NH)$NH_2$), amino, $C_{1-6}$ alkylamino, $C_{2-12}$ dialkylamino, and imidazyl;

$R_3$ is selected independently from the group including, but not limited to, phenyl, phenyl monosubstituted with K, phenyl disubstituted with K, phenyl trisubstituted with K, naphthyl, naphthyl monosubstituted with K, naphthyl disubstituted with K, naphthyl trisubstituted with K, $C_{1-10}$ alkenyl, $C_{3-15}$ cyclized alkyl, $C_{1-10}$ alkyl with a phenyl group attached to the $C_{1-10}$ alkyl, $C_{3-15}$ cyclized alkyl with an attached phenyl group, $C_{1-10}$ alkyl with an attached phenyl group monosubstituted with K, $C_{1-10}$ alkyl with an attached phenyl group disubstituted with K, $C_{1-10}$ alkyl with an attached phenyl group trisubstituted with K, $C_{3-15}$ cyclized alkyl with an attached phenyl group substituted with K, $C_{1-10}$ alkyl with a naphthyl group attached to the $C_{1-10}$ alkyl, $C_{3-15}$ cyclized alkyl with an attached naphthyl group, $C_{1-10}$ alkyl with an attached naphthyl group monosubstituted with K, $C_{1-10}$ alkyl with an attached naphthyl group disubstituted with K, $C_{1-10}$ alkyl with an attached naphthyl group trisubstituted with K, $C_{3-15}$ cyclized alkyl with an attached naphthyl group substituted with K;

or a pharmaceutically acceptable salt, pharmaceutically acceptable derivative, hydrate or solvate thereof.

Another embodiment of the present invention includes the above compounds with formula I, wherein the double bond carbons have stereochemistry selected from the group consisting of E and Z.

The following compounds are representatives of the invention:

Cbz-Ala-Phe-AS-Ph,

Cbz-Val-Phe-AS-Ph, and

Cbz-Leu-Phe-AS-Ph.

Methods of Preparation

1. Preparation of the Vinyl Sulfone Precursor

A) Preparation of the Phenyl Sulfonyl Phosphonate Precursor

The phenyl sulfonyl phosphonate precursor was prepared by reaction of diethyl phosphonate with chloromethyl phenyl sulfide with subsequent oxidation.

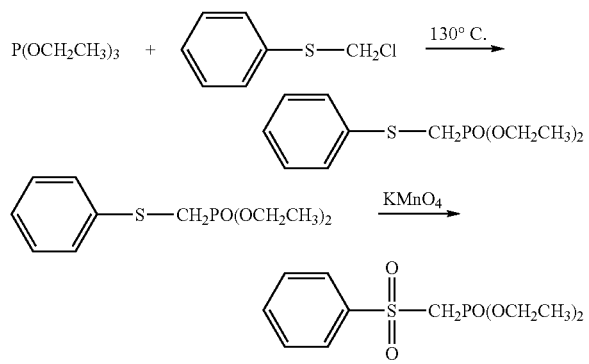

B) Preparation of the Aldehyde Precursor

The amino acid aldehyde precursor was prepared by formation of the Weinreb amide from a Boc-protected amino acid and N,O-dimethylhydroxylamine with subsequent reduction.

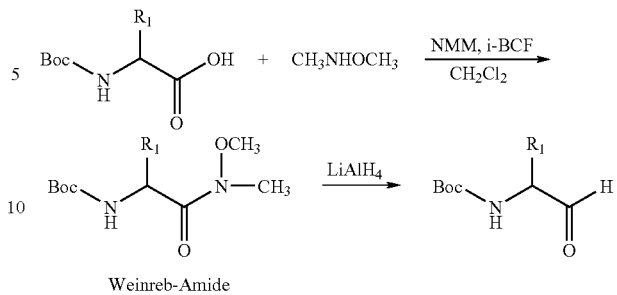

Weinreb-Amide

C) Horner-Wittig Coupling

The Boc-protected vinyl sulfone was prepared using a Wittig-Horner coupling from the amino acid aldehyde and the phosphonate precursor.

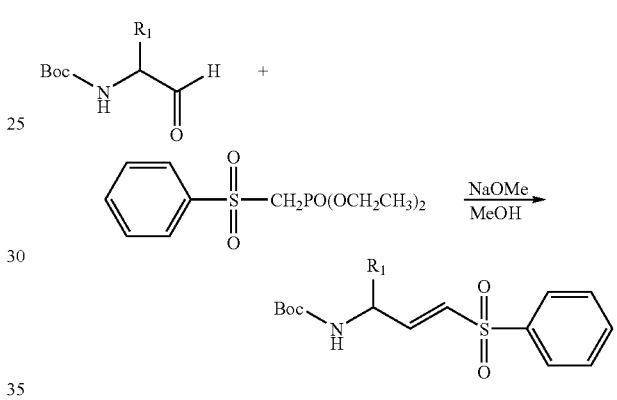

The peptide portion of the peptidyl aldehyde can be prepared using standard peptide chemistry which is well described in publications such as *The Peptides, Analysis, Synthesis, Biology*, Vol. 1-9, published in 1979-1987 by Academic Press; Houben-Weyl Methoden der Organischen Chemie, Vol. 15, Parts 1 and 2, *Synthese von Peptiden*, published by Georg Thieme Verlag, Stuttgart in 1974; and Houben-Weyl Methods of Organic Chemistry, Vol. E22, Parts a, b, c, and d, *Synthesis of Peptides and Peptidomimetics* published by Georg Thieme Verlag, Stuttgart 2000-2003 (references incorporated herein by reference).

The $M_1$ group can be introduced using a number of different reaction schemes. First, it could be introduced directly on an amino acid as shown in the following scheme (top), or the $M_1$ group could be introduced by reaction with an amino acid ester, followed by removal of the ester group to give the same product (bottom).

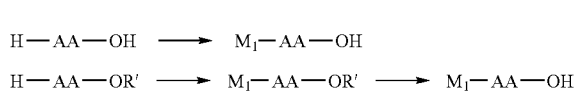

The techniques for introduction of the $M_1$ group are well documented in The Peptides, Houben-Weyl, and many other textbooks on organic synthesis. For example, reaction with cyanate or p-nitrophenyl cyanate would introduce a carbamyl group ($M_1$=$NH_2CO$—). Reaction with $Me_2NCOCl$ would introduce the $Me_2NCO$— group. Reaction with p-nitrophenyl thiocarbamate would introduce a thio carbamyl group ($M_1$=$NH_2CS$—). Reaction with $NH_2SO_2Cl$ would introduce the $NH_2SO_2$— group. Reaction with $Me_2NSO_2Cl$ would introduce the $Me_2NSO_2$— group. Reaction with a substituted alkyl or aryl isocyanate would introduce the X—NH—CO— group, where X is a substituted alkyl or aryl group. Reaction with a substituted alkyl or aryl isothiocyanate would introduce the X—NH—CS— group, where X is a substituted alkyl or aryl group. Reaction with X—$SO_2$—Cl would introduce the X—$SO_2$— group. Reaction with a substituted alkyl or aryl acid chloride would introduce an acyl group (M=X—CO—). For example, reaction with MeO—CO—$CH_2CH_2$—CO—Cl would give the X—CO— group, where X is a $C_2$ alkyl substituted with a $C_1$ alkyl-OCO— group. Reaction with a substituted alkyl or aryl thioacid chloride would introduce a thioacyl group (M=X—CS—). Reaction with a substituted alkyl or aryl sulfonyl chloride would introduce the X—$SO_2$— group. For example, reaction with dansyl chloride would give the X—$SO_2$— derivative, where X was a naphthyl group mono substituted with a dimethylamino group. Reaction with a substituted alkyl or aryl chloroformate would introduce the X—O—CO— group. Reaction with a substituted alkyl or aryl chlorothioformate would introduce the X—O—CS— group. There are many alternate reaction schemes which could be used to introduce all of the above $M_1$ groups to give either $M_1$-AA-OH or $M_1$-AA-OR'.

The $M_1$-AA-OH derivatives could then be used directly in the preparation of peptidyl vinyl sulfones or could be converted into the dipeptides, tripeptides, and tetrapeptides $M_1$-AA-AA-OH, $M_1$-AA-AA-AA-OH, or $M_1$-AA-AA-AA-AA-OH, which could then be converted to peptidyl allyl sulfones. The substituted peptides $M_1$-AA-AA-OH, $M_1$-AA-AA-AA-OH, or $M_1$-AA-AA-AA-AA-OH could also be prepared directly from H-AA-AA-OH, H-AA-AA-AA-OH, or H-AA-AA-AA-AA-OH using the reactions described above for introduction of the $M_1$ group. Alternatively, the $M_1$ group could be introduced by reaction with carboxyl blocked peptides to give $M_1$-AA-AA-OR', $M_1$-AA-AA-AA-OR', or $M_1$-AA-AA-AA-AA-OR', followed by the removal of the blocking group R'.

2. Preparation of the Peptidyl Allyl Sulfones

The peptidyl vinyl sulfone precursors were converted into peptidyl allyl sulfones using strong basic conditions. The reaction times can be reduced by adding a peroxidizing agent. An exemplary reaction is shown below.

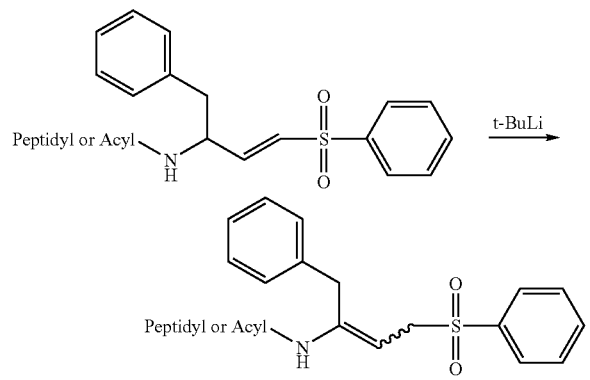

3. Synthetic Procedures and Examples

A) Material and Methods

Boc and Z-protected amino acid precursors were purchased from Bachem Bioscience Inc., King of Prussia, Pa. Peptides were synthesized using standard coupling procedures such as the mixed anhydride method. The $^1$H NMR spectra were obtained using a Varian Mercury 400 MHz spectrometer. Electrospray ionization (ESI), fast-atom-bombardment (FAB) and high-resolution mass spectrometry were performed using Micromass Quattro LC and VG Analytical 70-SE instruments. Elemental analysis was performed by Atlantic Microlab Inc., Norcross, Ga.

B) Preparation of Peptidyl Vinyl and Allyl Sulfones

Exemplary proceedures for preparation of the compounds and compositions of the present disclosure, and precursors thereof, are set forth below.

General Procedure for the Mixed Anhydride Coupling.

N-Methylmorpholine was added to Boc-AA-OH or Cbz-AA-OH in $CH_2Cl_2$ at $-15°$ C. followed by isobutyl chloroformate. N-Methylmorpholine was added to a cooled solution ($-15°$ C.) of HCl.H-AA-VS-Ph in $CH_2Cl_2$. This solution was added to the Boc-AA-OH or Cbz-AA-OH mixture, which had been stirring at $-15°$ C. The mixture was continued to stir at $-15°$ C. for 30 minutes, then warmed to room temperature and continued to stir over night. The amount of solvent was doubled, then washed with citric acid (10%, 3×), saturated $NaHCO_3$ (3×), and brine (3×), and finally dried ($MgSO_4$). The solvent was evaporated.

Diethyl Phenylsulfonylmethanephosphonate ($PhSO_2CH_2PO(OEt)_2$).

A mixture of chloromethyl phenyl sulfide (3.2 g, 20 mmole) and triethyl phosphite (3.3 g, 20 mmole) was heated at 130-140° C. for 5 h. The resultant mixture was distilled under reduced pressure, and the starting materials were distilled out. The oily residue was diethyl phenylmercaptomethanephosphonate, yield 3.4 g (65%). $^1$H-NMR ($CDCl_3$) δ 1.2-1.3 (t, 6H, 2×$CH_3$), 3.1-3.2 (d, 2H, S—$CH_2$), 4.0-4.2 (m, 4H, 2×$CH_2$), 7.2-7.4 (m, 5H, Ph). Diethyl phenylsulfonylmethanephosphonate was prepared by oxidation of diethyl phenylmercaptomethanephosphonate with potassium permanganate, yield 55%. $^1$H-NMR ($CDCl_3$) δ 1.2-1.3 (t, 6H, 2×$CH_3$), 3.7-3.8 (d, 2H, $SO_2$—$CH_2$), 4.1-4.2 (m, 4H, 2×$CH_2$), 7.5-7.7 (m, 3H, Ph), 7.9-8.0 (d, 2H, Ph). MS m/z 293 (M+1).

2-(tert-Butoxycarbonylamino)-3-phenylpropionaldehyde (Boc-Phe-H).

Boc-Phe-N($OCH_3$)$CH_3$ was prepared from Boc-Phe-OH and N,O-dimethylhydroxylamine hydrochloride using standard mixed anhydride coupling procedure, yield 93%. $^1$H-NMR ($CDCl_3$) δ 1.4 (s, 9H, Boc), 2.8-2.9 (m, 1H, $CH_2$-Phe), 3.0-3.1 (m, 1H, $CH_2$-Phe), 3.2 (s, 3H, N—$CH_3$), 3.6 (s, 3H, O—$CH_3$), 4.9 (m, 1H, α-H), 5.2 (b, 1H, NH), 7.1-7.3 (m, 5H, Ph). MS (FAB$^+$) m/z 309 (M+1, 30%), 253 (M−tBu+1, 100%). Reduction of Boc-Phe-N($OCH_3$)$CH_3$ with lithium aluminum hydride according to a previous method described in J. A. Fehrentz et al., Synthesis (1983), 8, 676 gave Boc-Phe-H, yield 88%. $^1$H-NMR ($CDCl_3$) δ 1.4 (s, 9H, Boc), 3.1 (d, 2H, $CH_2$-Phe), 4.4 (m, 1H, α-H), 5.0 (b, 1H, NH), 7.1-7.3 (m, 5H, Ph), 9.6 (s, 1H, CHO). MS (FAB$^+$) m/z 250 (M+1, 15%), 150 (M−Boc+1, 100%).

Phenyl-(3S)-3-amino-4-phenylbut-1-enyl Sulfone Hydrochloride (Phe-VS-Ph.HCl). Boc-Phe-VS-Ph was prepared by reaction of Boc-Phe-H with diethyl phenylsulfonylmethanephosphonate in the presence of 2 N sodium methoxide, yield 85%. $^1$H-NMR ($CDCl_3$) δ 1.3-1.4 (s, 9H, Boc), 2.9 (d, 2H, $CH_2$-Phe), 4.4-4.5 (b, 1H, α-H), 4.6-4.7 (b, 1H, NH), 6.3 (d, 1H, CH=), 6.9-7.0 (dd, 1H, CH=), 7.1-7.3 (m, 5H, Ph), 7.5-7.8 (m, 5H, $SO_2$-Ph). MS (FAB$^+$) m/z 388 (M+1, 15%), 288 (M−Boc+1, 100%). Boc-Phe-VS-Ph was deblocked with 6.7 N HCl in EtOAc to give Phe-VS-Ph.HCl, yield 88%. $^1$H-NMR (DMSO-$d_6$) δ 2.9-3.0 (m, 1H, $CH_2$-Phe), 3.1-3.2

(m, 1H, CH$_2$-Phe), 4.2 (b, 1H, α-H), 6.7-6.8 (m, 2H, CH=), 7.1-7.3 (m, 6H, CH= and Ph), 7.6-7.8 (m, 5H, SO$_2$-Ph), 8.6-8.8 (b, 2H, NH$_2$). MS (FAB$^+$) m/z 288 (M−Cl, 100%).

D-Phe-VS-Ph.HCl, white solid, 85% yield

Phenyl-(3S)-3-(N-carbobenzyloxyleucyl)amino-4-phenylbut-1-enyl Sulfone (Cbz-Leu-Phe-VS-Ph).

Cbz-Leu-Phe-VS-Ph was prepared from Cbz-Leu-OH and Phe-VS-Ph.HCl using standard mixed anhydride coupling method, yield 82%. $^1$H-NMR (CDCl$_3$) δ 0.8-0.9 (2d, 6H, 2×Leu-CH$_3$), 1.4-1.6 (m, 2H, Leu-CH$_2$), 2.06 (m, 1H, Leu-CH), 2.9-3.0 (m, 2H, CH$_2$-Phe), 3.9-4.0 (m, 1H, α-H), 4.8-4.9 (b, 1H, NH), 4.9-5.0 (m, 1H, α-H), 5.1 (m, 2H, Cbz) 6.3-6.4 (d & b, 2H, NH and CH=), 6.9-7.0 (dd, 1H, CH=), 7.1-7.4 (m, 10H, 2×Ph), 7.5-7.7 (m, 5H, SO$_2$-Ph). MS (ESI) m/z 535.

Cbz-Ala-Phe-VS-Ph, white solid, 88% yield.
Cbz-Val-Phe-VS-Ph, white solid, 98% yield.
Cbz-Leu-D-Phe-VS-Ph, white solid, 81% yield.

Phenyl-3-(N-carbobenzyloxyleucyl)amino-4-phenylbut-2-enyl Sulfone (Cbz-Leu-Phe-AS-Ph)

Butyllithium (3.63 ml, 6.17 mmol, 1.7 M in pentane) was added dropwise to a solution of tert-butylhydroperoxide (2.55 ml, 8.42 mmol, 3.3 M in toluene) in freshly distilled THF (80 ml) at −78° C. under argon. A solution of Cbz-Leu-Phe-VS-Ph (3.00 g, 5.61 mmol) in dry THF (30 ml) was added dropwise. The reaction was continued to stir at −20° C. for 45 minutes (TLC Hex/EtOAc 1:1). The reaction was quenched with saturated aqueous ammonium chloride (50 ml) and allowed to warm to room temperature. The organic layer was separated, and the aqueous layer was extracted with ethyl acetate (3×30 ml). The extracts were then washed with aqueous sodium sulfite (10%, 3×20 ml). The combined organic layers were dried (MgSO$_4$) and evaporated to give Cbz-Leu-Phe-AS-Ph as a white powder, yield 63%. $^1$H-NMR (CDCl$_3$) δ 0.8-0.9 (2d, 6H, 2×Leu-CH$_3$), 1.4-1.6 (m, 2H, Leu-CH$_2$), 3.8 (s, 2H, CH$_2$-Phe), 3.9 (d, 2H, CH$_2$—SO$_2$), 4.1 (m, 1H, α-H), 4.8 (t, 1H, CH=), 4.9-5.0 (b, 1H, NH), 5.1 (m, 2H, Cbz), 7.1-7.4 (m, 10H, 2×Ph), 7.5-7.7 (m, 5H, SO$_2$-Ph), 8.4 (b, 1H, NH). $^{13}$C NMR (400 MHz, CDCl$_3$) δ 172.1, 156.3, 144.4, 140.8, 135.7, 134.2, 133.6, 131.2, 129.5, 129.4×2, 129.3, 128.8×2, 128.7, 128.6, 128.4, 128.3, 127.8, 127.3, 126.9, 106.3, 67.6, 56.0, 55.6, 41.7, 40.4, 22.1, 21.0, 18.4. MS (FAB$^+$) m/z 535 (M+1, 100%). Anal. Calcd. for C$_{30}$H$_{34}$N$_2$O$_5$S: C, 67.39; H, 6.56; N, 5.43. Found: C, 67.41; H, 6.56; N, 5.43.

Cbz-Leu-Phe-AS-Ph (derived from Cbz-Leu-D-Phe-VS-Ph) white solid, 15% yield.
Cbz-Val-Phe-AS-Ph white solid, 21% yield.
Cbz-Ala-Phe-AS-Ph, white solid, 93% yield.

Methods of Use of Compounds of the Present Disclosure

Peptide allyl sulfones are irreversible inhibitors for cysteine proteases. We show that peptide allyl sulfones containing aliphatic side chains in the P2 site are excellent inhibitors of clan CA cysteine proteases. These structures may be used in vivo to treat diseases such as cancer and neurodegenerative diseases, which result from the uncontrolled proteolysis by cathepsins and calpains, and related cysteine proteases. These inhibitors may be used in vitro to prevent proteolysis, which occurs in the process of production, isolation, purification, storage, or transport of peptides and proteins. These inhibitors may be useful as therapeutic agents for treatment of neurodegeneration, viral infections, muscular dystrophy, myocardial tissue damage, tumor metastasis, and bone resorption. These structures may be used in vivo to treat parasitic infections such as sleeping sickness or Chagas' disease.

1. Enzyme Assays.

Papain and Cathepsin B Assays.

The incubation method was used to measure the irreversible inhibition of papain and cathepsin B. With cathepsin B, 30 µL of a stock inhibitor solution was added to 300 µL of a 0.1 M potassium phosphate buffer containing 1.25 mM EDTA, 0.01% Brij 35 at pH 6.0, followed by the addition of 30 µL of a freshly prepared cathepsin B solution (approximate concentration 6.98×10$^{-3}$ µg/µL) in the same potassium phosphate buffer containing 1 mM DTT (freshly prepared). Aliquots (50 µL) from the inhibition mixture were withdrawn at various time intervals and added to 200 µL of a 0.1 M potassium phosphate buffer containing 1.25 mM EDTA, 0.01% Brij 35 at pH 6.0, and the substrate Cbz-Arg-Arg-AMC (499 µM). The release of 7-amino-4-methylcoumarin was monitored ($\lambda_{ex}$=360 nm, $\lambda_{em}$=465 nm) using a Tecan Spectra Fluor microplate reader. Pseudo first-order inactivation rate constants were obtained from plots of ln v$_t$/v$_o$ versus time.

The incubation method was also used for commercially available papain. The inhibition incubation buffer for papain was 50 mM Hepes buffer at pH 7.5, containing 2.5 mM DTT (dithiothreitol) and 2.5 mM EDTA. The assay used the substrate Cbz-Phe-Arg-pNA (53.7 µM) in the same buffer. The approximate concentration of papain added to the incubation buffer was 0.29 mg/mL. The release of p-nitroanilide was monitored at 405 nm with a Molecular Devices Thermomax microplate reader. All assays were run in duplicate.

Calpain Assays.

Calpain I was purchased from Calbiochem (La Jolla, Calif.) in a solution of 30% glycerol at a concentration of 6.96 µM and stored at −20° C. prior to use. The calpain I assay was conducted with 235 µL of a solution of 50 mM Hepes, 0.5 M CaCl$_2$, 0.5 M cysteine, at pH 7.5 (calpain I buffer), 6.5 µL of Suc-Leu-Tyr-AMC substrate solution in DMSO and 4.2 µL of the enzyme solution (6.96 µM) at 23° C. The enzymatic activity was monitored by following the change in fluorescence for 10 min at 465 nm. The k$_2$ values were obtained by non-linear regression analysis and corrected for substrate (1+[S]/K$_M$=1.274). All assays were run in duplicate and the standard deviation was determined.

Cathepsin L Assays.

Cathepsin L was purchased from Athens Research & Technology (Athens, Ga.) in a 20 mM malonate buffer solution at pH 5.5 with 1 mM EDTA and 400 mM NaCl with a specific activity of 4.133 U/mg. The progress of cathepsin L inhibition was conducted with 243 µL of a solution of 0.25 M NaAc, 2 mM EDTA, 0.015% Brij, 5 mM DTT (dithiothreitol) at pH 5.5, 4 µL of Cbz-Phe-Arg-AMC substrate solution (16 mM) in DMSO (2% final concentration). Activity was monitored by following the change in fluorescence for 20 min at 465 nm. The k$_{obs}$ values were obtained by non-linear regression analysis and corrected for substrate (1+[S]/K$_M$=1.274). All assays were run in duplicate and the standard deviation was determined.

Cruzain and Rhodesain IC$_{50}$ Determinations.

Inhibitors were screened for effectiveness against purified recombinant cruzain and rhodesain. Cruzain (2 nM) or rhodesain (3 nM) was incubated with 0.0001 to 1 µM inhibitor in 100 mM sodium acetate buffer, pH 5.5 and 5 mM DTT (buffer A), for 5 minutes at room temperature. Buffer A containing Cbz-Phe-Arg-AMC (Bachem, K$_M$=1 µM, AMC=7-amino-4-methylcoumarin) was added to the enzyme and inhibitor to give 20 or 10 µM substrate concentration for cruzain and rhodesain, respectively, in 200 μL. The increase in fluorescence (excitation at 355 nm and emission at 460 nm) was followed with an automated microtiter plate spectrofluorimeter (Molecular Devices, Flex Station). Inhibitor stock solutions were prepared at 20 mM in DMSO and serial dilutions were made in DMSO (0.7% DMSO in assay). Controls were performed using enzyme alone, and enzyme with DMSO. $IC_{50}$ values were determined graphically using inhibitor concentrations in the linear portion of a plot of enzyme activity versus log [I] (7 concentrations tested with at least 2 in the linear range).

Table 1 shows the inhibitory constants ($k_{obs}/[I]$ or $IC_{50}$) for the inhibition of calpain I, papain, cathepsin B and L, cruzain and rhodesain. The inhibition constants $k_{obs}/[I]$ are pseudo-first order rate constants and the inhibitors with the higher numbers are more potent. The inhibition constants $IC_{50}$ represent the inhibitory concentration at which the inhibitor inactivates 50% of the enzyme. The lower the $IC_{50}$ the more potent is the inhibitor.

allyl double bond. There are several factors, which can contribute to a mixed ratio of isomers, such as the so-called "syn-effect" and the chelating lithium metal. This explains the difference in inhibitor potency between Cbz-Leu-Phe-AS-Ph (Isomer A), which is derived from the vinyl sulfone precursor Cbz-Leu-L-Phe-VS-Ph, and Cbz-Leu-Phe-AS-Ph (Isomer B). The initial stereochemistry of the phenylalanine side chain probably plays a significant role in the final ratio of Z to E isomers in the allyl sulfone inhibitor. The difference in potency of the two isomers is also observed with inhibition of cruzain and rhodesain. However, in this case the ranking is reversed. The Cbz-Leu-Phe-AS-Ph (Isomer A), which is derived from the vinyl sulfone precursor Cbz-Leu-L-Phe-VS-Ph, is more potent ($IC_{50}$=0.06 μM for cruzain and 0.04 μM for rhodesain) than isomer B ($IC_{50}$=0.3 μM for cruzain and 0.18 μM for rhodesain).

The novel allyl sulfone inhibitors Cbz-Leu-Phe-AS-Ph (both isomers) are more potent than the corresponding vinyl sulfone Cbz-Leu-Phe-VS-Ph; thus, these allyl sulfone inhibi-

TABLE 1

Inhibition of Clan CA Proteases by Peptidyl Allyl Sulfones.

| Inhibitor | $k_{obs}/[I] (M^{-1} s^{-1})^a$ | | | | $IC_{50} (\mu M)^b$ | |
| --- | --- | --- | --- | --- | --- | --- |
| | Calpain I[c] | Papain[d] | Cathepsin B[e] | Cathepsin L[e] | Cruzain | Rhodesain |
| Cbz-Ala-Phe-AS-Ph | 3 ± 0 | 9 ± 0 | N.I.[f] | 183 ± 10[g] | >10 | >10 |
| Cbz-Val-Phe-AS-Ph | 3 ± 0 | 6 ± 1 | N.I. | 310 ± 52[g] | 6 | 5 |
| Cbz-Leu-Phe-AS-Ph (Isomer A)[h] | 23 ± 4 | 49 ± 6 | N.I. | 700 ± 43[g] | 0.06 | 0.04 |
| Cbz-Leu-Phe-AS-Ph (Isomer B)[i] | 564 ± 32[g] | 15 ± 1 | N.I. | 1060 ± 121[g] | 0.3 | 0.18 |
| Cbz-Leu-Phe-VS-Ph | 550 ± 2[g] | 10 ± 0 | N.I. | 219 ± 96[g] | 2 | 0.5 |

[a]$k_{obs}$ is the pseudo first order rate constant obtained from plots of ln $v_t/v_0$ vs time unless indicated otherwise.
[b]Cruzain (2 nM) or rhodesain (3 nM) was incubated with 0.0001 to 1 μM inhibitor in 100 mM sodium acetate buffer, pH 5.5 and 5 mM DTT (buffer A), for 5 minutes at room temperature prior to substrate addition.
[c]Calpain I assay conditions: Irreversible kinetic assays were performed by the incubation method with calpain I from porcine erythrocytes. Enzymatic activities of calpain I were measured at 23° C. in 50 mM Hepes buffer (pH 7.5) containing 10 mM cysteine and 5 mM $CaCl_2$.
[d]Papain assay conditions: Incubation kinetics were measured using an enzyme stock solution for the papain assays, which was freshly prepared from 330 μL of enzyme storage solution (1.19 mg/mL) diluted with 645 μL papain buffer (50 mM Hepes, and 2.5 mM EDTA at pH 7.5) and 25 μL of DTT (0.1 M).
[e]Cathepsin B and L assay conditions: Enzymatic activities of cathepsin B were measured by the incubation method in 0.1 M $KHPO_4$, 1.25 mM EDTA, 0.01% Brij, pH 6.0 buffer and at 23° C.
[f]N.I. = no inhibition after 20 minutes of incubation.
[g]$k_{obs}$ is obtained by the progress curve method and corrected for substrate.
[h]Allyl sulfone is derived from the L-isomer of phenylalanine.
[i]Allyl sulfone is derived from the D-isomer of phenylalanine.

Peptidyl allyl sulfones show moderate inactivation rates with calpain and papain, and faster rates of inactivation with rhodesain and cruzain. The dipeptidyl allyl sulfones do not inhibit cathepsin B and show limited rates with both calpain I and papain. In contrast are the striking second order inhibition rate constant ($k_{obs}/[I]$) values of 564 $M^{-1}s^{-1}$ and 1062 $M^{-1}s^{-1}$ for Cbz-Leu-Phe-AS-Ph (Isomer B) with calpain I and cathepsin L, respectively. This dipeptidyl allyl sulfone was synthesized from the dipeptidyl vinyl sulfone precursor Cbz-Leu-D-Phe-VS-Ph. When the double bond isomerizes, the original Z stereochemistry of the vinyl sulfone is lost and the product has an unknown ratio of E to Z isomers at the new tors will likely be more effective inhibitors for treating various disorders. Allyl sulfone inhibitors of the present disclosure provide effective inhibitors of cystine proteases, in particular clan CA cystine proteases, such as cruzain and rhodesain. The effectiveness of the allyl sulfone inhibitors of the present disclosure may be further increased by modifications to the peptide sequence and the P' sulfonyl substituent.

Mechanism of Inhibition.

One mechanism for the inhibition reaction could involve re-isomerisation of the peptidyl allyl sulfone to the vinyl sulfone. This isomerization could be catalyzed by the active site histidine and would be reflected by a higher inhibition rate ($k_{obs}$/[I]) for the parent vinyl sulfone inhibitor. However, as the parent vinyl sulfone Cbz-Leu-Phe-VS-Ph was less potent with papain ($k_{obs}$/[I]=10 $M^{-1}s^{-1}$) than the corresponding allyl sulfone Cbz-Leu-Phe-AS-Ph (Isomer A) ($k_{obs}$/[I]= 49 $M^{-1}s^{-1}$) it is believed that the mechanism of inhibition does not involve re-isomerisation of the allyl sulfone to the vinyl sulfone with a subsequent attack of the cysteine thiol on the Michael acceptor double bond. This was even more pronounced with cruzain and rhodesain, where the same vinyl sulfone was over 30 fold and 12 fold less potent with cruzain ($IC_{50}$=2 µM) and rhodesain ($IC_{50}$=0.5 µM), respectively, than the corresponding allyl sulfone Cbz-Leu-Phe-AS-Ph. With calpain I it is possible that the isomerization mechanism is occurring, since the vinyl sulfone is aneffective inhibitor of calpain.

Two other mechanisms can be envisaged for enzyme inhibition by allyl sulfones (Scheme below). The active site cysteine could directly displace phenyl sulfinic acid in an $S_N2$ reaction (pathway b) or could attack the allylic double bond with loss of phenyl sulfinic acid (pathway a). Both pathways result in alkylation of the active site cysteine residue. It has previously been reported that allyl sulfones, when reacted with nucleophiles, undergo a tosyl elimination or displacement process, in which the allyl sulfone moiety undergoes alkylation at either the α- or γ-carbon. An alternative possibility for enzyme inactivation follows a mechanism-based pathway, which is initiated by removal of the amide nitrogen proton by a base or the active site histidine, followed by the elimination of phenyl sulfinic acid and the formation of the imine (Structure bottom left). The active site cysteine then reacts with the imine in a Michael addition, which also irreversibly alkylates the enzyme.

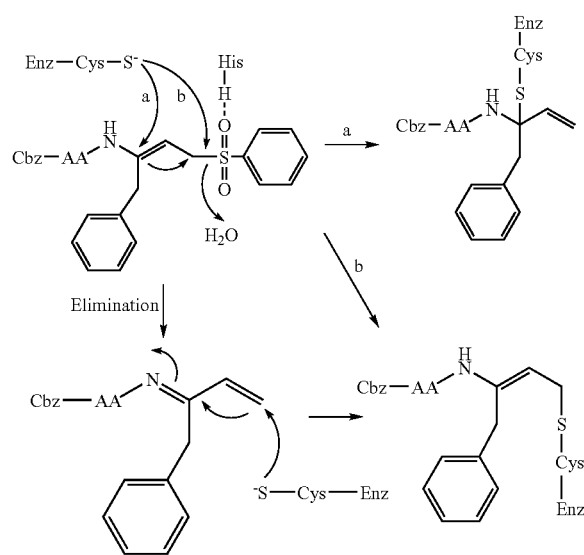

The peptide allyl sulfone derivatives, as shown above, bind to the enzymes using many of the interactions that are found in complexes of a particular enzyme with its substrates and/or inhibitors. Additional interactions with the enzyme can be obtained by tailoring the $R_3$ group of the inhibitor to imitate the amino acid residues, which are preferred by an individual protease at the S1 40 and S2' subsites. For example, peptidyl allyl sulfones with $R_3$ phenylalkyl groups would interact effectively with cruzain, which is shown to prefer such structures in vinyl sulfone peptide inhibitors. Likewise, the $M_1$ group can interact with the S subsites of the target cysteine protease. Once a good inhibitor structure for a particular enzyme is found, it is then possible to change other characteristics such as solubility or hydrophobicity by adding substituents to the $M_1$ or $R_1$, $R_2$, $R_3$, and $R_4$ groups.

The following structures are exemplary peptidyl allyl sulfone inhibitors for the listed enzymes. The inhibitor sequences were derived from peptide substrate and/or inhibitor sequences in the protease literature.

| | |
|---|---|
| Ac-Leu-Leu-Met($O_2$)-AS-Ph | for calpain I and II |
| Cbz-Leu-Leu-Hph-AS-Ph | for calpain I and II |
| Ac-Leu-Leu-Met-AS-Ph | for cruzain |
| Mu-Phe-Lys-AS-Ph | for cathepsin S |
| Mu-2Np-Hph-AS-EtPh | for cathepsin L |
| Mu-Np2-Hph-AS-2Np | for cathepsin B |
| Cbz-Phe-Hph-AS-Ph | for rhodesain |
| Cbz-Leu-Leu-Leu-AS-EtPh | for papain |
| Cbz-Leu-Leu-Leu-AS-Ph | for calpain |
| Ala-Hph-AS-Ph | for DPPI (cathepsin C) |
| Lys(biotinyl)-Hph-AS-Ph | for DPPI (cathepsin C) |
| 4-Morpholine-CO-Phe-Hph-AS-Ph | cruzain |
| Cbz-Phe-Hph-AS-$CH_2$-Ph | cruzain |
| N-Methylpiperidine-CO-Leu-Hph-AS-Ph | cathepsin V |
| N-Methylpiperazine-CO-Leu-Hph-AS-Ph | cathepsin V |
| Piperazine-CO-Leu-Hph-AS-Ph | cathepsin K |

2. In Vitro Uses.

To use the above inhibitors in vitro, they are dissolved in an organic solvent such as dimethylsulfoxide or ethanol, and are added to an aqueous solution containing serine and/or cysteine proteases. The final concentration of the organic solvent should be less than 25%. The inhibitors may also be added as solids or in suspension. The cysteine protease inhibitors of this invention would be useful in a variety of experimental procedures where proteolysis is a significant problem. Inclusion of these inhibitors in radioimmunoassay experiments would result in higher sensitivity. The use of these inhibitors in plasma fractionation procedures would result in higher yields of valuable plasma proteins and would make purification of the proteins easier. The inhibitors disclosed here could be used in cloning experiments utilizing bacterial cultures, yeast, and human cells to produce a purified cloned product in higher yield.

The novel compounds of this disclosure are effective in the prevention of unnecessary proteolysis caused by cysteine proteases in the process of purification, transport and storage of peptides and proteins as shown, for example, in Table 1 by effective inhibition of many cysteine proteases.

Diagnostic Reagents

Peptidyl allyl sulfones of the present disclosure can be used for the identification of proteases, for example novel cysteine proteases. One embodiment provides a method for screening a sample for the presence of a protease, particularly a cysteine protease, by contacting the sample with a peptidyl allyl sulfone, for example a peptidyl allyl sulfone of Formula I, and detecting the presence of the peptidyl allyl sulfone-protease conjugate. Detection of the conjugate may be accomplished using known techniques. For example, peptidyl allyl sulfones of the present invention can be modified with a detectable label including but not limited to a radioisotope, fluorescent marker, biotin, antibody, enzyme conjugate such as horseradish peroxidase, or the like. The peptidyl allyl sulfone conjugates can be fixed to a support, for example using known chemical fixatives, and a sample can then by added to the peptidyl allyl sulfone. Such support can be microarrays or the like. The fixed peptidyl allyl sulfone can then irreversibly or reversibly bind a protease, for example a cysteine protease, in the sample. The support can be washed to remove excess sample. The peptidyl allyl sulfone-protease conjugate can then be eluted from the support and the protease can be detected or identified using conventional techniques. The support can be any durable substance including but not limited to metal, plastic, glass, quartz or the like. The peptidyl allyl sulfone can be linked to the support with a linker, for example a cleavable linker to facilliate the removal of peptidyl allyl sulfone-protease conjugates.

3. In Vivo Uses.

Effective inhibitors of the proteolytic function of clan CA enzymes (Table 1) can be used to treat a variety of diseases. Cathepsins are involved in a variety of disease states, including progressive cartilage and bone degradation associated with arthritis. Inhibitors of these cathepsins have reduced inflammation and prevented joint destruction in animal models of arthritis. Thus, effective inhibitors of cathepsins can be used for the treatment of arthritis. Cathepsins B and L have been linked to metastasis and invasion by cancer cells. Peptidyl allyl sulfones, which inhibit cathepsin B and L, can therefore be used as thereaputic agents for cancer.

Infection of mammals and man by the protozoan parasite *Trypanosoma cruzi* results in Chagas' disease, which causes heart disease. One target for treatment that has received significant attention is cruzain, the major cysteine protease found in *T. cruzi*. Peptidyl allyl sulfones are potent inhibitors of cruzain and can therefore effectively treat Chagas' disease.

Rhodesain is a cysteine protease vital for the development of the parasite *Trypanosoma brucei rhodensiense*, which upon infection causes sleeping sickness in humans and cattle. Inhibitors for the cysteine protease rhodesain can thus prevent parasite development and treat and/or prevent sleeping sickness.

Calpains have been implicated in a variety of physiological disorders, such as neurodegeneration in Alzheimer's, Parkinson's, and Huntington's disease, spinal injury and muscular dystrophy and other neurodegenerative disorders, including, but not limited to, stroke, multiple scelrosis, neurophathies, dentatorubropallidoluuysian astrophy, spinocerebellar atrophy type 3, spinal bulbar muscular atrophy, peripheral neuropathy, and myotrophic lateral sclerosis. Other diseases include cardiac ischemia, cataract formation, thromolytic platelet aggregation, restenosis, joint inflammation and arthritis. The ability of peptidyl allyl sulfones to inhibit calpains can therefore be applied in the treatment of the above disorders.

4. Drug Delivery.

This disclosure also provides a pharmaceutical composition, which comprises a compound according to Formula I and a pharmaceutically accepted carrier, diluent or excipient. Accordingly, the compounds of Formula I may be used in the manufacture of a medicament. For therapeutic use, the peptidyl allyl sulfones may be administered orally, topically, or parenterally. The term parenteral, as used, includes subcutaneous injection, intravenous, intramuscular, intrasternal injection, or infusion techniques. The therapeutically effective amount, and thus the appropriate dosage depends primarily on the specific formulation and on the object of the therapy or prophylaxis. The amount of the individual doses as well as the administration is best determined by individually assessing each case.

The pharmaceutical compositions containing the active ingredient may be in a form suitable for oral use, for example, as tablets, troches, lozenges, aqueous or oily suspensions, dispersible powders or granules, emulsions, hard or soft capsules, syrups, or elixirs. Dosage levels of the order of 0.2 mg to 140 mg per kilogram of body weight per day are useful in the treatment of the above-indicated conditions (10 mg to 7 gms per patient per day). The amount of active ingredient that may be combined with carrier materials to produce a single dosage form will vary depending upon the host treated and the particular mode of administration.

For injection, the therapeutic amount of the peptidyl allyl sulfones or their pharmaceutically acceptable salts will normally be in the dosage range from 0.2 to 140 mg/kg of body weight. Administration is generally made by intravenous, intramuscular, or subcutaneous injection. Accordingly, pharmaceutical compositions for parenteral administration will contain from about 10 mg to 7 gms of the compounds per dose. In addition to the active ingredient, these pharmaceutical compositions may also contain a buffer, e.g. a phosphate buffer, which keeps the pH in the range from about 3.5 to 7, and a compound such as sodium chloride, mannitol, or sorbitol for adjusting the isotonic pressure.

A composition for topical application can be formulated as an aqueous solution, lotion, jelly or an oily solution or suspension. A composition in the form of an aqueous solution is obtained by dissolving the compounds of this invention in aqueous buffer solution of about pH 4 to 6.5 and, if desired, adding a polymeric binder. An oily formulation for topical application is obtained by suspending the compounds of this invention in an oil, optionally with the addition of a swelling agent such as aluminium stearate and/or a surfactant.

EXAMPLES

The following detailed examples are given to illustrate the present disclosure and are not intended to limit it in any manner.

Example 1

Diethyl Phenylsulfonylmethanephosphonate ($PhSO_2CH_2PO(OEt)_2$). A mixture of chloromethyl phenyl sulfide (3.2 g, 20 mmole) and triethyl phosphite (3.3 g, 20 mmole) was heated at 130-140° C. for 5 h. The resultant mixture was distilled under reduced pressure, and the starting materials were distilled out. The oily residue was diethyl phenylmercaptomethanephosphonate, yield 3.4 g (65%). $^1$H-NMR (CDCl$_3$) δ 1.2-1.3 (t, 6H, 2×CH$_3$), 3.1-3.2 (d, 2H, S—CH$_2$), 4.0-4.2 (m, 4H, 2×CH$_2$), 7.2-7.4 (m, 5H, Ph). Diethyl phenylsulfonylmethanephosphonate was prepared by oxidation of diethyl phenylmercaptomethanephosphonate with potassium permanganate, yield 55%. $^1$H-NMR (CDCl$_3$) δ 1.2-1.3 (t, 6H, 2×CH$_3$), 3.7-3.8 (d, 2H, SO$_2$—CH$_2$), 4.1-4.2 (m, 4H, 2×CH$_2$), 7.5-7.7 (m, 3H, Ph), 7.9-8.0 (d, 2H, Ph). MS m/z 293 (M+1).

Example 2

2-(tert-Butoxycarbonylamino)-3-phenylpropionaldehyde (Boc-Phe-H).

General Procedure for the Mixed Anhydride Coupling.

N-Methylmorpholine was added to Boc-AA-OH or Cbz-AA-OH in CH$_2$Cl$_2$ at −15° C. followed by isobutyl chloroformate. N-Methylmorpholine was added to a cooled solution (−15° C.) of HCl.H-AA-VS-Ph or N,O dimethylhydroxylamine hydrochloride in CH$_2$Cl$_2$. This solution was added to the Boc-AA-OH or Cbz-AA-OH mixture, which had been stirring at −15° C. The mixture was continued to stir at −15° C. for 30 minutes, then warmed to room temperature and continued to stir over night. The amount of solvent was doubled, then washed with citric acid (10%, 3×), saturated NaHCO$_3$ (3×), and brine (3×), and finally dried (MgSO$_4$). The solvent was evaporated.

Boc-Phe-N(OCH$_3$)CH$_3$ was prepared from Boc-Phe-OH and N,O-dimethylhydroxylamine hydrochloride using standard mixed anhydride coupling procedure, yield 93%. $^1$H-NMR (CDCl$_3$) δ 1.4 (s, 9H, Boc), 2.8-2.9 (m, 1H, CH$_2$-Phe), 3.0-3.1 (m, 1H, CH$_2$-Phe), 3.2 (s, 3H, N—CH$_3$), 3.6 (s, 3H, O—CH$_3$), 4.9 (m, 1H, α-H), 5.2 (b, 1H, NH), 7.1-7.3 (m, 5H, Ph). MS (FAB$^+$) m/z 309 (M+1, 30%), 253 (M−tBu+1, 100%). Reduction of Boc-Phe-N(OCH$_3$)CH$_3$ with lithium aluminum hydride according to a previously described method gave Boc-Phe-H, yield 88%. $^1$H-NMR (CDCl$_3$) δ 1.4 (s, 9H, Boc), 3.1 (d, 2H, CH$_2$-Phe), 4.4 (m, 1H, α-H), 5.0 (b, 1H, NH), 7.1-7.3 (m, 5H, Ph), 9.6 (s, 1H, CHO). MS (FAB$^+$) m/z 250 (M+1, 15%), 150 (M−Boc+1, 100%).

Example 3A

Phenyl-(3S)-3-amino-4-phenylbut-1-enyl Sulfone Hydrochloride (Phe-VS-Ph.HCl). Boc-Phe-VS-Ph was prepared by reaction of Boc-Phe-H with diethyl phenylsulfonylmethanephosphonate in the presence of 2 N sodium methoxide, yield 85%. $^1$H-NMR (CDCl$_3$) δ 1.3-1.4 (s, 9H, Boc), 2.9 (d, 2H, CH$_2$-Phe), 4.4-4.5 (b, 1H, α-H), 4.6-4.7 (b, 1H, NH), 6.3 (d, 1H, CH═), 6.9-7.0 (dd, 1H, CH═), 7.1-7.3 (m, 5H, Ph), 7.5-7.8 (m, 5H, SO$_2$-Ph). MS (FAB$^+$) m/z 388 (M+1, 15%), 288 (M−Boc+1, 100%). Boc-Phe-VS-Ph was deblocked with 6.7 N HCl in EtOAc to give Phe-VS-Ph.HCl, yield 88%. $^1$H-NMR (DMSO-d$_6$) δ 2.9-3.0 (m, 1H, CH$_2$-Phe), 3.1-3.2 (m, 1H, CH$_2$-Phe), 4.2 (b, 1H, α-H), 6.7-6.8 (m, 2H, CH═), 7.1-7.3 (m, 6H, CH═ and Ph), 7.6-7.8 (m, 5H, SO$_2$-Ph), 8.6-8.8 (b, 2H, NH$_2$). MS (FAB$^+$) m/z 288 (M−Cl, 100%).

Example 3B

Phenyl-(3R)-3-amino-4-phenylbut-1-enyl Sulfone Hydrochloride (D-Phe-VS-Ph.HCl). Boc-D-Phe-VS-Ph was prepared by reaction of Boc-D-Phe-H with diethyl phenylsulfonylmethanephosphonate in the presence of 2 N sodium methoxide, yield 85%. $^1$H-NMR (CDCl$_3$) δ 1.3-1.4 (s, 9H, Boc), 2.9 (d, 2H, CH$_2$-Phe), 4.4-4.5 (b, 1H, α-H), 4.6-4.7 (b, 1H, NH), 6.3 (d, 1H, CH═), 6.9-7.0 (dd, 1H, CH═), 7.1-7.3 (m, 5H, Ph), 7.5-7.8 (m, 5H, SO$_2$-Ph). MS (FAB$^+$) m/z 388 (M+1, 15%), 288 (M−Boc+1, 100%). Boc-D-Phe-VS-Ph was deblocked with 6.7 N HCl in EtOAc to give D-Phe-VS-Ph.HCl, yield 88%. $^1$H-NMR (DMSO-d$_6$) δ 2.9-3.0 (m, 1H, CH$_2$-Phe), 3.1-3.2 (m, 1H, CH$_2$-Phe), 4.2 (b, 1H, α-H), 6.7-6.8 (m, 2H, CH═), 7.1-7.3 (m, 6H, CH═ and Ph), 7.6-7.8 (m, 5H, SO$_2$-Ph), 8.6-8.8 (b, 2H, NH$_2$). MS (FAB$^+$) m/z 288 (M−Cl, 100%).

Example 4A

Phenyl-(3S)-3-(N-carbobenzyloxyleucyl)amino-4-phenylbut-1-enyl Sulfone (Cbz-Leu-Phe-VS-Ph). Cbz-Leu-Phe-VS-Ph was prepared from Cbz-Leu-OH and Phe-VS-Ph.HCl using standard mixed anhydride coupling method, yield 82%. $^1$H-NMR (CDCl$_3$) δ 0.8-0.9 (2d, 6H, 2×Leu-CH$_3$), 1.4-1.6 (m, 2H, Leu-CH$_2$), 2.06 (m, 1H, Leu-CH), 2.9-3.0 (m, 2H, CH$_2$-Phe), 3.9-4.0 (m, 1H, α-H), 4.8-4.9 (b, 1H, NH), 4.9-5.0 (m, 1H, α-H), 5.1 (m, 2H, Cbz) 6.3-6.4 (d & b, 2H, NH and CH═), 6.9-7.0 (dd, 1H, CH═), 7.1-7.4 (m, 10H, 2×Ph), 7.5-7.7 (m, 5H, SO$_2$-Ph). MS (ESI) m/z 535.

Example 4B

Phenyl-(3R)-3-(N-carbobenzyloxyleucyl)amino-4-phenylbut-1-enyl Sulfone (Cbz-Leu-D-Phe-VS-Ph). Cbz-Leu-D-Phe-VS-Ph was prepared from Cbz-Leu-OH and D-Phe-VS-Ph.HCl using standard mixed anhydride coupling method, yield 81%. $^1$H-NMR (CDCl$_3$) δ 0.8-0.9 (2d, 6H, 2×Leu-CH$_3$), 1.4-1.6 (m, 2H, Leu-CH$_2$), 2.06 (m, 1H, Leu-CH), 2.9-3.0 (m, 2H, CH$_2$-Phe), 3.9-4.0 (m, 1H, α-H), 4.8-4.9 (b, 1H, α-H), 4.9-5.0 (m, 1H, NH), 5.1 (m, 2H, Cbz), 6.3-6.4 (d & b, 2H, NH and CH═), 6.9-7.0 (dd, 1H, CH═), 7.1-7.4 (m, 10H, 2×Ph), 7.5-7.7 (m, 5H, SO$_2$-Ph). MS (ESI) m/z 535.

Example 4C

Phenyl-(3S)-3-(N-carbobenzyloxyvalyl)amino-4-phenylbut-1-enyl Sulfone (Cbz-Val-Phe-VS-Ph). Cbz-Val-Phe-VS-Ph was prepared from Cbz-Val-OH and Phe-VS-Ph.HCl using standard mixed anhydride coupling method, yield 98%. $^1$H-NMR (CDCl$_3$) δ 0.70-0.84 (2d, 6H, Val-CH$_3$), 2.06 (m, 1H, Val-CH), 2.91 (m, 2H, CH$_2$-Phe), 3.82 (m, 1H, α-H), 4.80-4.90 (m, 1H, α-H), 5.10 (s, 2H, Cbz), 5.96 (d, 1H, NH) 6.34 (d, 1H, CH═), 6.9-7.0 (dd, 1H, CH═), 7.1-7.4 (m, 10H, 2×Ph), 7.5-7.7 (m, 5H, SO$_2$-Ph). MS (ESI) m/z 521 (M+1, 100%).

Example 4D

Phenyl-(3S)-3-(N-carbobenzyloxyalanyl)amino-4-phenylbut-1-enyl Sulfone (Cbz-Ala-Phe-VS-Ph). Cbz-Ala-Phe-VS-Ph was prepared from Cbz-Ala-OH and Phe-VS-Ph.HCl using standard mixed anhydride coupling method, yield 88%. $^1$H-NMR (CDCl$_3$) δ 1.25 (d, 3H, Ala-CH$_3$), 2.91 (dq, 2H, CH$_2$-Phe), 4.10 (m, 1H, α-H), 4.80-4.90 (m, 1H, α-H), 5.10 (s, 2H, Cbz), 6.34 (b, 1H, NH), 6.39 (d, 1H, CH═), 6.90-6.98 (dd, 1H, CH═), 7.10-7.39 (m, 10H, 2×Ph), 7.55 (t, 2H, SO$_2$-Ph), 7.65 (t, 1H, SO$_2$-Ph), 7.91 (d, 2H, SO$_2$-Ph). $^{13}$C NMR (400 MHz, CDCl$_3$) δ 172.1, 156.3, 144.4, 140.8, 135.7, 134.2, 133.6, 131.2, 129.5, 129.4×3, 129.3, 128.8×2, 128.7, 128.6, 128.4, 128.3, 127.8, 127.3, 126.9, 67.6, 51.7, 51.6, 40.2, 19.4.

Example 5A

Phenyl-3-(N-carbobenzyloxyleucyl)amino-4-phenylbut-2-enyl Sulfone (Cbz-Leu-Phe-AS-Ph). Butyllithium (3.63 ml, 6.17 mmol, 1.7 M in pentane) was added dropwise to a solution of tert-butylhydroperoxide (2.55 ml, 8.42 mmol, 3.3 M in toluene) in freshly distilled THF (80 ml) at −78° C. under argon. A solution of Cbz-Leu-Phe-VS-Ph (3.00 g, 5.61 mmol) in dry THF (30 ml) was added dropwise. The reaction was continued to stir at −20° C. for 45 minutes (TLC Hex/EtOAc 1:1). The reaction was quenched with saturated aqueous ammonium chloride (50 ml) and allowed to warm to room temperature. The organic layer was separated, and the aqueous layer was extracted with ethyl acetate (3×30 ml). The extracts were then washed with aqueous sodium sulfite (10%, 3×20 ml). The combined organic layers were dried (MgSO$_4$) and evaporated to give Cbz-Leu-Phe-AS-Ph as a white powder, yield 63%. $^1$H-NMR (CDCl$_3$) δ 0.8-0.9 (2d, 6H, 2×Leu-CH$_3$), 1.4-1.6 (m, 2H, Leu-CH$_2$), 3.8 (s, 2H, CH$_2$-Phe), 3.9 (d, 2H, CH$_2$—SO$_2$), 4.1 (m, 1H, α-H), 4.8 (t, 1H, CH═), 4.9-5.0 (b, 1H, NH), 5.1 (m, 2H, Cbz), 7.1-7.4 (m, 10H, 2×Ph), 7.5-7.7 (m, 5H, SO$_2$-Ph), 8.4 (b, 1H, NH). $^{13}$C NMR (400 MHz, CDCl$_3$)δ 172.1, 156.3, 144.4, 140.8, 135.7, 134.2, 133.6, 131.2, 129.5, 129.4×2, 129.3, 128.8×2, 128.7, 128.6, 128.4, 128.3, 127.8, 127.3, 126.9, 106.3, 67.6, 56.0, 55.6, 41.7, 40.4, 22.1, 21.0, 18.4. MS (FAB$^+$) m/z 535 (M+1, 100%). Anal. Calcd. for $C_{30}H_{34}N_2O_5S$: C, 67.39; H, 6.56; N, 5.43. Found: C, 67.41; H, 6.56; N, 5.43.

Example 5B

Phenyl-3-(N-carbobenzyloxyleucyl)amino-4-phenylbut-2-enyl Sulfone (Cbz-Leu-Phe-AS-Ph) (Isomer B). Cbz-Leu-D-Phe-VS-Ph was treated with butyllithium and tert-butylhydroperoxide in freshly distilled THF as described with Cbz-Leu-Phe-VS-Ph above to give Cbz-Leu-Phe-AS-Ph (Isomer B) as a white powder, yield 15%. $^1$H-NMR (CDCl$_3$) δ 0.8-0.9 (2d, 6H, 2×Leu-CH$_3$), 1.4-1.6 (m, 2H, Leu-CH$_2$), 2.06 (m, 1H, Leu-CH), 3.8 (s, 2H, CH$_2$-Phe), 3.9 (d, 2H, CH$_2$—SO$_2$), 4.1 (m, 1H, α-H), 4.8 (t, 1H, CH=), 4.9-5.0 (b, 1H, NH), 5.1 (m, 2H, Cbz), 7.1-7.4 (m, 10H, 2×Ph), 7.5-7.7 (m, 5H, SO$_2$-Ph); 8.4 (b, 1H, NH). MS (ESI) m/z 535 (M+1, 100%). Anal. calcd. for $C_{30}H_{34}N_2O_5S$: C, 67.39; H, 6.56; N, 5.43. Found: C, 67.12; H, 6.61; N, 5.33.

Example 5C

Phenyl-3-(N-carbobenzyloxyvalyl)amino-4-phenylbut-2-enyl Sulfone (Cbz-Val-Phe-AS-Ph). Cbz-Val-Phe-VS-Ph was treated with butyllithium and tert-butylhydroperoxide in freshly distilled THF as described with Cbz-Leu-Phe-VS-Ph above to give Cbz-Val-Phe-AS-Ph as a white powder, yield 21%. $^1$H-NMR (CDCl$_3$) δ 0.70-0.85 (2d, 6H, Val-CH$_3$), 2.1 (m, 1H, Val-CH), 3.80 (d, 2H, CH$_2$-Phe), 3.95 (m, 3H, CH$_2$—SO$_2$ and α-H), 4.90 (t, 1H, CH=), 5.12 (m, 3H, NH and Cbz), 7.1-7.4 (m, 10H, 2×Ph), 7.55 (t, 2H, SO$_2$-Ph), 7.65 (t, 1H, SO$_2$-Ph), 7.91 (d, 2H, SO$_2$-Ph), 8.42 (b, 1H, NH). $^{13}$C NMR (300 MHz, CDCl$_3$) δ 172.1, 156.3, 144.4, 140.8, 135.7, 134.2, 133.6, 131.2, 129.5, 129.4×2, 129.3, 128.8×2, 128.7, 128.6, 128.4, 128.3, 127.8, 127.3, 126.9, 106.3, 67.6, 56.0, 55.6, 41.7, 22.0, 21.0, 18.4. MS (FAB$^+$) m/z 521 (M+1, 100%). Anal. calcd. for $C_{29}H_{32}N_2O_5S$.1/10 H$_2$O: C, 66.67; H, 6.21; N, 5.36. Found: C, 66.31; H, 6.23; N, 5.26.

Example 5D

Phenyl-3-(N-carbobenzyloxyalanyl)amino-4-phenylbut-2-enyl Sulfone (Cbz-Ala-Phe-AS-Ph). Cbz-Ala-Phe-VS-Ph was treated with butyllithium and tert-butylhydroperoxide in freshly distilled THF, as described with Cbz-Leu-Phe-VS-Ph above, to give Cbz-Ala-Phe-AS-Ph as a white powder, yield 93%. $^1$H-NMR (CDCl$_3$) δ 1.21 (d, 3H, Ala-CH$_3$), 3.80 (m, 4H, CH$_2$-Phe and CH$_2$—SO$_2$), 4.12 (q, 1H, α-H), 4.88 (t, 1H, CH=), 5.11 (m, 3H, NH and Cbz), 7.30 (m, 10H, 2×Ph), 7.50 (t, 2H, SO$_2$-Ph), 7.64 (t, 1H, SO$_2$-Ph), 7.83 (d, 2H, SO$_2$-Ph), 8.40 (b, 1H, NH). $^{13}$C NMR (400 MHz, CDCl$_3$) δ 172.1, 156.3, 144.4, 140.8, 135.7, 134.2, 133.6, 131.2, 129.5, 129.4×2, 129.3, 128.8×2, 128.7, 128.6, 128.4, 128.3, 127.8, 127.3, 126.9, 107.2, 67.6, 51.7, 51.6, 40.2, 19.4. MS (FAB$^+$) m/z 493 (M+1, 100%). HRMS calcd. for $C_{27}H_{29}N_2O_5S$: 493.17972. Obsd. 493.17663. Anal. calcd. for $C_{27}H_{28}N_2O_5S$: C, 65.83; H, 5.73; N, 5.69. Found: C, 65.73; H, 5.82; N, 5.68.

The above specification and Examples fully disclose how to make and use the compounds of the present disclosure. However, the present disclosure is not limited to the particular embodiments described hereinabove, but includes all modifications thereof within the scope of the following claims. The various references to journals, patents, and other publications, which are cited herein comprise the state of the art and are incorporated herein by reference.

What is claimed is:

1. A compound of the formula:

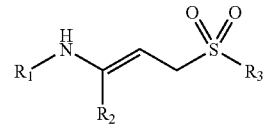

wherein,
$R_1$ is selected from the group consisting of phenyl-O—CO— and phenyl-O—CO—AA$_1$;
AA$_1$, is an aliphatic amino acid with the L configuration, D configuration, or no chirality at the alpha-carbon, wherein AA$_1$ is selected from the group consisting of alanine, valine, leucine, isoleucine, norleucine, and norvaline,
$R_2$ is $C_{1-10}$ alkyl substituted with phenyl;
$R_3$ is selected independently from the group consisting of phenyl, phenyl monosubstituted with K, phenyl disubstituted with K, phenyl trisubstituted with K, $C_{1-10}$ alkyl with a phenyl group attached to the $C_{1-10}$ alkyl, $C_{1-10}$ alkyl with an attached phenyl group monosubstituted with K, $C_{1-10}$ alkyl with an attached phenyl group disubstituted with K, $C_{1-10}$ alkyl with an attached phenyl group trisubstituted with K,
K is selected from the group consisting of halogen, $C_{1-10}$ alkyl, $C_{1-10}$ perfluoroalkyl, $C_{1-10}$ alkoxy, phenoxy, NO$_2$, CN, OH, CO$_2$H, CONH$_2$, amino, $C_{1-10}$ alkylamino, $C_{2-12}$ dialkylamino, $C_{1-10}$ acyl, and $C_{1-10}$ alkoxy-CO—, and $C_{1-10}$ alkyl-S—;
or a pharmaceutically acceptable salt, hydrate or solvate thereof.

2. The compound of claim 1, wherein the double bond carbons have stereochemistry selected from the group consisting of cis, trans, E, and Z.

3. The compound of claim 1, wherein:
AA$_1$ is selected from the group consisting of alanine, valine, and leucine;
$R_2$ is $C_1$ alkyl substituted with phenyl; and
$R_3$ is phenyl.

4. The compound of claim 1, wherein:
$R_1$ is phenyl-O—CO—;
$R_2$ is $C_1$ alkyl substituted with phenyl; and
$R_3$ is phenyl.

5. The compound of claim 1, wherein the compound is selected from the group consisting of Cbz-Ala-Phe-AS-Ph, Cbz-Val-Phe-AS-Ph, and Cbz-Leu-Phe-AS-Ph, wherein AS is an allyl sulfone.

6. The compound of claim 1, wherein the compound is Cbz-Phe-AS-Ph, wherein AS is an allyl sulfone.

7. The compound of claim 1, wherein said compound specifically inhibits cysteine proteases.

8. A pharmaceutical composition comprising an effective amount of a compound of claim 1.

9. The pharmaceutical composition of claim 8, further comprising a pharmaceutically acceptable carrier.

* * * * *